United States Patent
Gueniche et al.

(10) Patent No.: US 9,770,474 B2
(45) Date of Patent: Sep. 26, 2017

(54) BACTERIAL EXTRACTS CULTURED IN THERMAL WATERS COMPRISING ANTI-REDNESS AGENTS

(75) Inventors: Audrey Gueniche, Rueil Malmaison (FR); Lionel Breton, Versailles (FR)

(73) Assignee: L'Oreal, Paris (FR)

(*) Notice: Subject to any disclaimer, the term of this patent is extended or adjusted under 35 U.S.C. 154(b) by 1444 days.

(21) Appl. No.: 12/175,108

(22) Filed: Jul. 17, 2008

(65) Prior Publication Data

US 2009/0028805 A1 Jan. 29, 2009

Related U.S. Application Data

(60) Provisional application No. 60/935,007, filed on Jul. 20, 2017.

(30) Foreign Application Priority Data

Jul. 17, 2007 (FR) ...................................... 07 56532

(51) Int. Cl.
| | | |
|---|---|---|
| *A01N 65/00* | (2009.01) | |
| *A61K 35/74* | (2015.01) | |
| *A61K 8/99* | (2017.01) | |
| *A61K 35/08* | (2015.01) | |
| *A61Q 1/02* | (2006.01) | |
| *A61Q 19/00* | (2006.01) | |

(52) U.S. Cl.
CPC ............... *A61K 35/74* (2013.01); *A61K 8/99* (2013.01); *A61K 35/08* (2013.01); *A61Q 1/02* (2013.01); *A61Q 19/004* (2013.01)

(58) Field of Classification Search
CPC ..................................................... A61K 36/00
USPC .......................................................... 424/725
See application file for complete search history.

(56) References Cited

U.S. PATENT DOCUMENTS

| | | |
|---|---|---|
| 4,419,449 A | 12/1983 | Maillard et al. |
| 5,795,574 A | 8/1998 | Breton et al. |
| 5,895,649 A * | 4/1999 | De Lacharriere et al. |
| 6,190,671 B1 | 2/2001 | Aubert et al. |
| 2009/0022819 A1 | 1/2009 | Gueniche et al. |
| 2009/0028826 A1 | 1/2009 | Breton et al. |
| 2009/0136604 A1 | 5/2009 | Breton et al. |

FOREIGN PATENT DOCUMENTS

| | | | |
|---|---|---|---|
| DE | 102004012135 A1 * | 9/2005 | |
| FR | 2 693 654 A1 | 1/1994 | |
| FR | 2 700 172 A1 | 7/1994 | |
| FR | 2 746 646 A1 | 10/1997 | |

OTHER PUBLICATIONS

Mahe et al., "Induction of the skin endogenous protective mitochondrial MnSOD by *Vitreoscilla filiformis* extract", Int'l Journal of Cosmetic Science, 2006, pp. 277-287, vol. 28.
Gueniche et al., "Improvement of atopic dermatitis skin symptoms by *Vitreoscilla filiformis* bacterial extract", Eur. J. Dermatol., 2006, pp. 380-384, vol. 16.
XP009091787, 2006 ESDR Abstracts #578, www.jidonline.org.
XP009091787, 2006 ESDR Abstracts #578, www.jidonline.org, Aug. 2006 (with Table of Contents).
Copending U.S. Appl. No. 12/175,072, naming Audrey Gueniche et al. as inventors and filed Jul. 17, 2008.
Copending U.S. Appl. No. 12/175,119, naming Lionel Breton et al. as inventors and filed Jul. 17, 2008.
Copending U.S. Appl. No. 12/175,129, naming Lionel Breton et al. as inventors and filed Jul. 17, 2008.

* cited by examiner

*Primary Examiner* — Michael Meller
(74) *Attorney, Agent, or Firm* — Buchanan Ingersoll & Rooney PC

(57) ABSTRACT

Red blotches on the skin such as those associated with environmental stresses, or red blotches associated with a skin disorder, for example those occurring during rosacea, are treated/reduced by administering to individuals afflicted therewith, thus effective amounts of at least one extract of a non-photosynthetic and non-fruiting filamentous bacterium cultured in a medium which includes at least one non-sulfurous mineral and/or thermal water, e.g., an extract derived from the bacterium *Vitreoscilla filiformis*, in particular the strain ATCC 15551, cultured in a medium enriched with water from La Roche Posay.

11 Claims, 1 Drawing Sheet

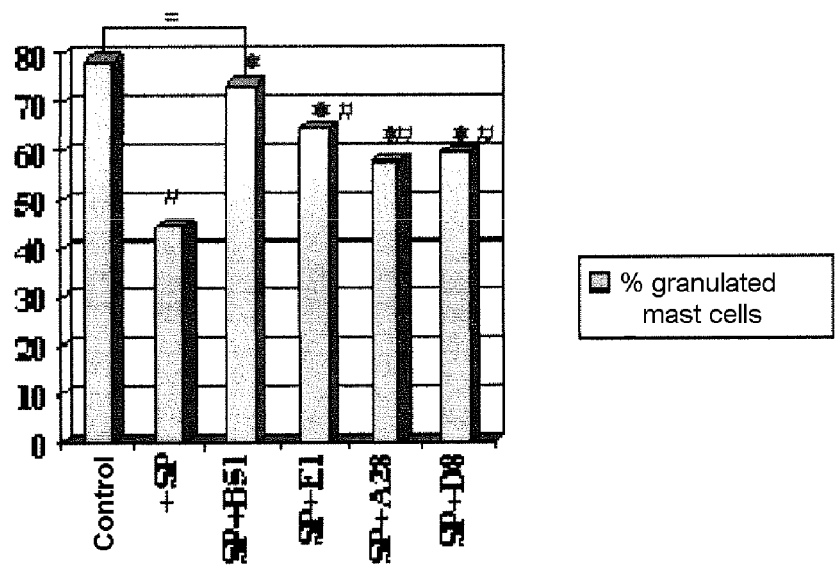
Histological evaluation after staining with toluidine blue of the percentage of mast cells having a score of 3 (mean, n = 8)

BACTERIAL EXTRACTS CULTURED IN THERMAL WATERS COMPRISING ANTI-REDNESS AGENTS

CROSS-REFERENCE TO COMPANION APPLICATIONS

Companion U.S. patent application Ser. No. 12/175,072; U.S. patent application Ser. No. 12/175,119; and U.S. patent application Ser. No. 12/175,129, filed concurrently herewith, each hereby also expressly incorporated by reference and each also assigned to the assignee hereof.

CROSS-REFERENCE TO PRIORITY/PROVISIONAL APPLICATIONS

This application claims priority under 35 U.S.C. §119 of FR 0756532, filed Jul. 17, 2007, and of U.S. Provisional Application No. 60/935,007, Jul. 20, 2007, each hereby expressly incorporated by reference and each assigned to the assignee hereof.

BACKGROUND OF THE INVENTION

Technical Field of the Invention

The present invention relates to the administration of bacterial extracts cultured on thermal water as agents for reducing red blotches on the skin, such as those related to environmental stresses, or even red blotches associated with a skin disorder, for example those occurring during rosacea.

Preferably, the bacterial extract is obtained from the bacterium *Vitreoscilla filiformis*, in particular the ATCC 15551 strain, cultured on a medium enriched with water from La Roche Posay.

Description of Background and/or Related and/or Prior Art

Rosacea is a pathological skin condition which manifests itself as four subtypes: erythematotelangiectactic, papullopustular, hypertrophic and ocular. In the vascular forms, the capillaries are dilated, the continuity of the endothelium being sometimes interrupted. This leads to a superficial oedema associated with perivascular and perifollicular inflammation of medium intensity. In total, the morphological elements suggest that the primum movens of the disease is a vascular impairment followed by an increase in colonization by the mite *Demodex*. French estimations are that the prevalence of this condition in the population is 3%, ⅔ of which are women.

Certain neuropeptides such as substance P or VIP contribute to the local inflammation phenomenon responsible for red blotches on the skin and in individuals suffering from rosacea. Thus, it remains useful to have a product which acts on the cutaneous phenomena linked to the release of substance P, thus making it possible to limit the amplifying action of substance P on the inflammatory "process" and to reduce the skin erythema in particular observed in individuals suffering from rosacea, atopical dermatitis or seborrheic dermatitis.

SUMMARY OF THE INVENTION

It has now been demonstrated that extracts of a non-photosynthetic and non-fruiting filamentous bacterium cultured on a medium comprising at least one non-sulfurous mineral and/or thermal water reduce red blotches on the skin.

It has more specifically been demonstrated that the treatment of a human skin explant under survival conditions with an extract of the *Vitreoscilla filiformis* bacterium cultured on a medium enriched with thermal water from La Roche Posay, protects the tissue against vasodilation induced by substance P.

Comparison of this effect with that of an extract of the same bacterium cultured on a comparable culture medium obtained with distilled water only shows that the bacterial extract used according to the invention has a greater effect.

Thus, the present invention features the administration/topical application of at least one extract of a non-photosynthetic and non-fruiting filamentous bacterium cultured on a medium comprising at least one non-sulfurous mineral and/or thermal water as an agent for preventing and/or limiting and/or correcting the appearance of red blotches on the skin.

BRIEF DESCRIPTION OF THE DRAWING

The FIGURE of Drawing illustrates histological evaluation after staining with toluidine blue of the percentage of mast cells having a score of 3 (mean, n=8).

DETAILED DESCRIPTION OF BEST MODE AND SPECIFIC/PREFERRED EMBODIMENTS OF THE INVENTION

Bacterial Extract:

The bacterial extracts according to the present invention are prepared according to a process comprising the culturing of at least one non-photosynthetic and non-fruiting filamentous bacterium in a medium comprising at least one non-sulfurous mineral and/or thermal water.

The bacteria are non-photosynthetic filamentous bacteria which comprise, in particular, the bacteria belonging to the order of the Beggiatoales and more particularly the bacteria belonging to the genera *Beggiatoa, Vitreoscilla, Flexithrix* or *Leucothrix*.

For implementing the invention, bacteria belonging to the genus *Vitreoscilla* are preferred, in particular bacteria of the species *Vitreoscilla filiformis*.

These bacteria, several of which have already been described, generally have an aquatic habitat and can be found in particular in sea waters or in thermal waters. Exemplary bacteria include:

*Vitreoscilla filiformis* (ATCC 15551)
*Vitreoscilla beggiatoides* (ATCC 43181)
*Beggiatoa alba* (ATCC 33555)
*Flexithrix dorotheae* (ATCC 23163)
*Leucothrix mucor* (ATCC 25107)
*Sphaerotilus natans* (ATCC 13338)

Preferably, the bacterium is that corresponding to the strain deposited at the ATCC under No. 15551.

The term "thermal water" means a hot or cold water which is used for its therapeutic powers or for a bathing use. It is possible to use a thermal water or a mineral water. Generally, a mineral water is suitable for consumption, which is not always the case with a thermal water. Each of these waters comprises, inter alia, dissolved minerals and trace elements. These waters are known to be employed for specific treatment purposes depending on the particular trace elements and minerals present therein.

Preferably, a thermal and/or mineral water is employed which exhibits a total mineral content of greater than or equal to 400 mg/l.

According to this invention, the term "total mineral content" means the sum of the concentrations of anions and cations present in the thermal or mineral water. In the thermal or mineral waters according to the invention, the total mineral content generally ranges from 400 to 900 mg/l.

The thermal and/or mineral water according to the invention can have a total mineral content of at least 700 mg/l, in particular a total concentration of carbonates and of bicarbonates of at least 150 mg/l and more preferably of at least 360 mg/l and in particular of sodium carbonate and bicarbonate of greater than 2 mg/l. The concentration of silicon oxide in the water used in the composition according to the invention can preferably be at least 6 mg/l and more preferably at least 9 mg/l.

The thermal water or the mineral water according to the invention can be selected from water from Vittel, waters from the Vichy basin, water from Uriage, water from La Roche Posay, water from La Bourboule, water from Enghien-les-Bains, water from Saint-Gervais-les-Bains, water from Néris-les-Bains, water from Allevard-les-Bains, water from Digne, water from Maiziéres, water from Neyrac-les-Bains, water from Lons-le-Saunier, water from Eaux-Bonnes, water from Rochefort, water from Saint Christau, water from Les Fumades and water from Tercis-les-Bains.

Among these waters, those which exhibit a total concentration of carbonates or bicarbonates of greater than 360 mg/l are water from Vittel, water from La Bourboule, water from Les Fumades, water from Enghien-les-Bains, water from La Roche Posay, water from the Vichy basin and water from Uriage.

Among these waters, those which exhibit a concentration of carbonates or bicarbonates of from 150 mg/l and 360 mg/l are water from Digne, water from Maiziéres, water from Rochefort or water from Saint Gervais-les-Bains.

Among these waters, those which comprise at least 2 mg/l of sodium carbonate or bicarbonate are water from La Roche Posay, water from Vittel, waters from the Vichy basin or water from Uriage.

The waters comprising at least 9 mg/l of silicon oxide are water from La Roche Posay, water from Vittel, waters from the Vichy basin or water from Uriage.

The thermal or mineral waters which are particularly suitable for the implementation of the invention have a concentration of calcium ions of greater than or equal to 100 mg/l, indeed even 140 mg/l.

According to one advantageous embodiment, the thermal or mineral water has a concentration of hydrogencarbonate ions of greater than or equal to 300 mg/l. The hydrogencarbonates, also known as bicarbonates, are present in particular at a concentration of greater than or equal to 350 mg/l.

According to another advantageous embodiment, the bacteria are cultured in a medium comprising at least one thermal water. The latter can in particular be selected from water from Vittel, waters from the Vichy basin, water from Uriage, water from La Roche Posay, water from La Bourboule, water from Les Fumades, water from Enghien-les-Bains or water from Eaux-Bonnes.

The waters which make it possible to obtain a particularly advantageous result according to the invention are selected in particular from water from La Roche Posay and water from Vittel, or a water with a similar composition.

Water from La Roche Posay is extracted from the spring of the same name; it is a water comprising bicarbonate, calcium, silicate and selenium. It generally comprises approximately 387 mg/l of bicarbonate ions, approximately 140 mg/l of calcium ions and at least 4 mg/l of sulfates.

Water from Vittel is rich in calcium and in mineral salts (841 mg/l) and comprises in particular 202 mg/l of calcium, 402 mg/l of bicarbonates and 336 mg/l of sulfates.

Culturing can in particular be carried out in the following medium:

| Composition: | Concentration: |
| --- | --- |
| Autolyzed yeast extract | 0.5 to 5 g/l |
| Plant peptone | 0.5 to 5 g/l |
| Anhydrous glucose | 0.5 to 7 g/l |
| Heller microelements | 0.5 to 5 ml/l |
| $CaCl_2 \cdot 10H_2O$ | 0.010 to 0.200 g/l |

The composition is made up to 1,000 ml with mineral and/or thermal water optionally topped with distilled or osmosed water.

Exemplary peptones include soybean papain peptone.

This medium is distinguished from the media generally used by the absence of catalase and sulfide.

The Heller microelements have been described by Heller, *Ann. Sci. Nat. Biol. Veg.*, 14, 1-223 (1953). They are mixtures of various mineral elements which are recommended by Heller not for the culturing of bacteria but for the nutrition of plant tissues cultured in vitro.

Culturing can be carried out at the appropriate temperature suitable for the bacterial species cultured. Generally, this temperature ranges from 18 and 40° C., depending on the strains. The pH of the culture medium preferably ranges from 5.5 to 8.

The composition of the Heller microelements, per 1 l of water, is as follows:

| | |
| --- | --- |
| $ZnSO_4 \cdot 7H_2O$ | 1 g |
| $MnSO_4 \cdot H_2O$ | 0.076 g |
| $CuSO_4 \cdot 5H_2O$ | 0.003 g |
| KI | 0.010 g |
| $H_3BO_3$ | 1 g |
| $AlCl_3 \cdot 6H_2O$ | 0.050 g |
| $NiCl_2 \cdot 6H_2O$ | 0.030 g |

Said thermal or mineral waters can replace all or part of the aqueous phase of the culture medium. They can thus be a mixture in any proportion with the water, in particular distilled or osmosed water, present in the culture medium. The mixture (i) of thermal water and (ii) of osmosed or distilled water could be in a ratio from 0.1% to 100%, especially from 0.1 to 50, in particular from 0.1 to 25.

After mixing all the elements of the medium, the culture medium comprising the thermal and/or mineral water is advantageously sterilized; this stage is carried out by methods known to one skilled in the art, such as sterilization by filtration or by heat.

The culture medium is subsequently inoculated with the bacteria.

The media most suitable for culturing bacteria are such that the thermal or mineral water preferably is at least 0.1% of the amount of water introduced for the preparation of the medium, in particular from 0.1 to 99.9%. Good results are obtained with concentrations of thermal water of approximately 1.33%, with respect to the osmosed and/or distilled water, for example from 0.5 to 20%, indeed even from 0.5 to 50%, but these concentrations can be increased without disadvantage.

In known fashion, the process for preparing the bacterial extract comprises at least one stage in which the bacteria are recovered at the end of culturing, in particular by separating them from the culture medium.

After culturing the bacteria, the biomass can be isolated by various known methods, for example by filtration, by coagulation with an alcohol (ethanol, isopropanol, isobutanol), by drying on a cylinder with a scraped precoat (starch, diatoms, and the like) or by freeze-drying. A preliminary concentration, for example at 80° C. under reduced pressure, improves this separation.

The biomass may be used alive or else be treated by various processes. An operation of rupturing the envelopes can be carried out, for example by the action of ultrasound. In addition, extracts can be prepared using an alcohol, such as ethanol or propanol.

Lipopolysaccharide extracts can also be prepared according to known methods; for example, see Noris and Ribbons, *Methods in Microbiology*, Vol. 5B, Academic Press (1971). The method generally used is the well-known "Westphal" method (or a related method), which consists in carrying out the extraction with phenol/water mixtures at 65° C. The extract is subsequently subjected to dialysis in order to remove the phenol.

The bacterial extract employed according to the invention may also result from the implementation of the following process: (i) at least one bacterium belonging to the order of the Beggiatoales is cultured in a medium comprising a monosaccharide as main carbon source and at least one mineral or thermal water and then (ii), after fermentation, the bacteria are separated from the culture medium in order to recover said mass of bacteria.

The bacteria recovered on conclusion of the fermentation stage can in particular be subjected to a stabilization and/or extraction treatment. It is the extract of filamentous bacteria which is thus obtained which will generally be used in or for the preparation of cosmetic or dermatological compositions. In a way known per se, the extract can thus be sterilized, in particular by filtration or by autoclaving.

The term "extract of non-photosynthetic filamentous bacteria" means equally well the supernatant from the culturing of said bacteria, the biomass obtained after culturing said bacteria or the extracts of the biomass which are obtained by treatment of this biomass.

In order to prepare the extracts according to the invention, said bacteria can be cultured according to the above process and can then be separated from the biomass obtained, for example by filtration, centrifuging, coagulation and/or freeze-drying.

Thus, after culturing, the bacteria are concentrated by centrifuging. The biomass obtained is autoclaved. This biomass can be freeze-dried in order to constitute what is referred to as the freeze-dried extract. Any freeze-drying method known to one skilled in the art can be used to prepare this extract.

The supernatant fraction from this biomass can also be filtered into a sterile container in order to remove the suspended particles. This supernatant fraction can also be decanted under sterile conditions into a sterile container. According to a specific embodiment of the invention, the supernatant fraction thus obtained is used as cosmetic or dermatological active principle.

The bacterial extracts according to the invention may be formulated in a suitable carrier in an amount of at least 20% by weight relative to the total weight of the composition, in particular in an amount of 0.001 to 20% by weight relative to the total weight of the composition and more particularly in an amount of 0.01 to 10% by weight relative to the total weight of the composition.

For certain applications or specific formulations, it may be advantageous to use high weight concentrations of bacterial extract, for example from 15 and 20%.

The bacterial extract cultured in a medium enriched with thermal water may also be used in the form of fractions of cellular components or in the form of metabolites. The microorganism(s), metabolite(s) or fraction(s) may also be introduced in the form of a freeze-dried powder, a culture supernatant and/or, where appropriate, in a concentrated form.

For certain applications, the living biomass may be used as is, for example in the form of masks or a poultice for producing an immediate effect.

According to the invention, the term "metabolite" is any substance derived from the metabolism of the microorganisms considered according to the invention and endowed with an efficacy for treating dark circles.

For the purpose of the invention, the term "metabolite" is any substance derived from the metabolism of the microorganisms under consideration according to the invention and which is effective in treating red blotches on the skin.

Unexpectedly, it has now been observed that the bacterial extracts cultured on thermal water could prove to be effective for the treatment of red blotches on the skin.

Indeed, it has now been demonstrated that the extract of the bacterium *Vitreoscilla filiformis* cultured on thermal water from La Roche Posay is more effective in the treatment of red blotches on the skin than the extract of the same bacterium cultured on a conventional medium, i.e., without mineral or thermal water.

The main difference from these two extracts is in the procedures for preparing the culture medium where there is substitution of osmosed water by water from La Roche Posay. This leads in particular to a modification of the metabolism of the bacteria caused by an enrichment of the culture medium in mineral elements, particularly in selenium, strontium and zinc.

It is also interesting to note that the introduction of this biomass into a formulatory carrier does not present a risk of overexposure to these elements, since Se and Zn are elements that are essential to the body and Sr is widespread in food.

The table below provides the concentrations of these chemical elements in the bacterial extract according to the invention prepared according to the procedure of Example 1 (freeze-dried extract).

| | |
|---|---|
| Se (mg/kg) | 6 |
| Sr (mg/kg) | 10 |
| Zn (mg/kg) | 216 |

Thus, the application of this enriched extract leads to topical exposures of mineral salts per day of around:

| | |
|---|---|
| Se (µg/day) | 0.008 |
| Sr (µg/day) | 0.0032 |
| Zn (µg/day) | 0.094 |

It is noted here that the use of ions for improving skin condition is very old. Thus, dermatologically-targeted thermal cures on the banks of the Dead Sea—the saltiest expanse of water in the world—go back to ancient times (Abels D J et col, *Clinics in Dermatol.*, 14: 653-658, 1996). These baths exert an anti-pruriginous activity and it is not uncommon that people treated experience the feeling of having smoother and more supple skin (Even-Pazz Z, Isr *J. Med. Sci.*, 32: 11-15, 1996). To date, the advantage of the topical application of cations has been studied as much in the field of sensitivity as in that of skin dryness. Among the divalent cations, it is the calming effect of strontium which has been most documented (Hahn G S, In biochemical modulation of skin reactions. Kydonieus A F, Will J J (eds.), CRE, Boca Raton, Fla., US, 261-272, 2000).

More specifically, the present invention features the cosmetic administration of at least one extract of a non-photosynthetic and non-fruiting bacterium cultured on a non-sulfurous mineral and/or thermal water, as an agent for treating red blotches on the skin.

The term "red blotch" means a pinkish to red, or even dark red, coloration of all or part of the skin of the body, the scalp, the mucous membranes or the semi-mucous membranes. This manifestation, also called erythema, which can be a sign of good health (rosy cheeks) is most commonly undesirable, in particular when it is associated with other symptoms of a skin disorder such as rosacea, atopic dermatitis or seborrheic dermatitis.

The term "treating", unless otherwise indicated, means any action for improving the comfort or the well-being of an individual; this term therefore equally covers preventing, reducing, relieving and curing.

This invention therefore features the administration of at least one extract of a non-photosynthetic and non-fruiting filamentous bacterium cultured on a medium comprising at least one non-sulfurous mineral and/or thermal water, as an agent for treating red blotches on the skin. This treatment may be directed towards both normal skin and skin which is the seat of a pathological condition exhibiting a disorder of the cutaneous vascular system.

More specifically, this invention features administration of the bacterial extract as an agent for the treatment of red blotches on the skin, flushes and paroxysmal erythema.

The present invention also features administration of at least one extract of a non-photosynthetic and non-fruiting filamentous bacterium cultured on a medium comprising at least one non-sulfurous mineral and/or thermal water, for embellishing the appearance of the skin and/or the mucous membranes, preventing and/or reducing the intensity of red blotches on the skin and/or slight skin oedema, lightening the complexion and/or making it uniform, and/or masking surface red blotches and/or fading out the signs of skin microcirculation, i.e., making less visible the blood capillaries that are noticeable, in particular on the face.

This invention also features administration of the extract of a non-photosynthetic and non-fruiting filamentous bacterium cultured on a medium comprising at least one non-sulfurous mineral and/or thermal water, for the treatment of red blotches from rosacea.

The present invention also features incorporating at least one extract of a non-photosynthetic and non-fruiting filamentous bacterium cultured on a medium comprising at least one non-sulfurous mineral and/or thermal water, into a composition useful for the treatment of red blotches associated with a pathological skin condition, for example red blotches from rosacea.

Rosacea is a common, chronic and progressive dermatosis related to vascular relaxation. It mainly affects the central part of the face and is characterized by redness of the face or hot flushes, facial erythema, papules, pustules and telangiectasia. In serious cases, particularly in men, the soft tissue of the nose may swell and produce a bulbous swelling known as rhinophyma.

Rosacea generally develops in four stages:

stage 1 of vascular relaxation having a neurogenic component (at about 20 years old). The patients experience sudden bursts of paroxysmal redness of the face and neck, with a hot sensation, but with no systemic signs. After the attacks, the skin of the face returns to normal. These "flushes" are triggered by changes in temperature (occasionally leading to thermophobia), and the intake of hot drinks or alcohol;

stage 2 of erythematotelangiectasia (at about 30 years old). The cheekbone areas are diffusely red. Dilated capillaries constituting standard acne rosacea are observed therein. Unlike stage 1, the redness is permanent. In addition to the cheeks, the chin and the middle of the forehead may be affected;

stage 3 of papulopustules (at about 40 years old). Papules and pustules a few millimeters in diameter develop on a background of erythema, without associated comedones. This dermatosis may be very extensive, occasionally up to the bald part of the scalp in men, but is absent from the area around the mouth and the eyes. The patients complain of sensitive skin, with subjective intolerance to the majority of topical products and greasy cosmetics;

stage 4 of rhinophyma (at about 50 years old or later). This later phase mainly affects men, unlike the other stages. The nose is increased in volume and diffusely red and the follicular orifices are dilated. The skin gradually thickens.

Administration according to the invention is particularly suitable for the treatment of the red blotches on the skin of the first stage of rosacea.

The present invention is also advantageous for the treatment of erythema of the skin caused by external agents, whether they are products capable of causing a skin irritation or atmospheric agents (exposure to light, to wind, to the cold, to dry air, to abrupt variations in temperature, etc.).

This invention also relates to the preparation of compositions for use in the treatment of sunburn, red blotches accompanying a burn, erythema associated with atopic dermatitis and erythema associated with seborrheic dermatitis.

The present invention therefore also features extracts of a non-photosynthetic and non-fruiting filamentous bacterium cultured on a medium comprising at least one non-sulfurous mineral and/or thermal water, for the treatment of sunburn, red blotches accompanying a burn, erythema associated with skin disorders, atopic dermatitis and/or erythema associated with seborrheic dermatitis.

According to a preferred embodiment of the invention, an effective amount of an extract of a non-photosynthetic and non-fruiting filamentous bacterium cultured on a medium comprising at least one non-sulfurous mineral and/or thermal water is used for the preparation of a composition for treating erythema associated with skin disorders, such as uticaria, eczematous dermatitis, psoriasis, herpes, photodermatoses, contact dermatitis, lichen, prurigos, pruriginous diseases, fibroses, collagen maturation disorders, scleroderma or eczema.

The present invention also features a cosmetic regime or regimen wherein an effective amount of at least one extract of a non-photosynthetic and non-fruiting filamentous bacterium cultured on a medium comprising at least one non-sulfurous mineral and/or thermal water is applied to the skin and/or the scalp and/or the mucous membranes and semi-mucous membranes.

In particular, it may be a cosmetic regime or regimen for preventing and/or fading out red blotches and/or the signs of skin microcirculation, characterized in that an effective amount of at least one extract of a non-photosynthetic and non-fruiting filamentous bacterium cultured on a medium comprising at least one non-sulfurous mineral and/or thermal water is topically applied onto the skin and/or the scalp and/or the mucous membranes and semi-mucous membranes.

The bacterial extracts according to the invention are used for the preparation of compositions, preferably topical compositions, for use in the treatment of skin disorders having an erythemal component, especially rosacea, in particular the first stage of rosacea.

Whatever its purpose, the bacterial extracts according to the invention are administered via the route most suitable for the desired effect, in particular orally or topically, preferably topically.

The term "topically" means an administration of the extracts according to the invention or of the compositions containing the latter, by application onto the skin.

Unless otherwise indicated, the term "skin" means any cutaneous surface of the body including the skin and extended to the scalp and the mucous membranes and semi-mucous membranes, and the term "appendages" means the eyelashes, body hairs, head hair and nails.

The topical compositions according to the invention which are for use in treating the skin, the mucous membranes and semi-mucous membranes and the scalp may be in the form of a salve, creams, milks, ointments, powders, impregnated pads, solutions, gels, sprays, lotions or suspensions. They may also be in the form of lipid or polymeric vesicles or nanospheres or microspheres or polymeric patches and hydrogels for controlled release. These topical compositions may be either in an anhydrous form or in an aqueous form.

The compositions are in particular for use in hair hygiene. They may in particular be in the form of a cream, a milk, a lotion, a gel, lipid or polymeric vesicles or nanospheres or microspheres, a soap or a shampoo.

In the compositions according to the invention, the extract of a non-photosynthetic and non-fruiting filamentous bacterium cultured on a non-sulfurous mineral and/or thermal water is advantageously used in combination with retinoids or corticosteroids, or combined with free-radical scavengers, with alpha-hydroxy or alpha-keto acids or derivatives thereof, or else ion channel blockers.

The dermocosmetic compositions according to the invention may also contain inert or even pharmacodynamically or cosmetically active additives or combinations of these additives, and in particular: wetting agents, depigmenting agents such as hydroquinone, azelaic acid, caffeic acid or kojic acid; emollients; moisturizers such as glycerol, PEG-400 or urea; anti-seborrheic or anti-acneic agents, such as S-carboxymethylcysteine, S-benzylcysteamine, their salts and their derivatives, or benzoyl peroxide; antibiotics such as erythromycin and its esters, neomycin, clindamycin and its esters, tetracyclines; anti-fungal agents such as ketoconazole or 4,5-polymethylene-3-isothiazolinones; agents for promoting hair regrowth, such as minoxidil (2,4-diamino-6-piperidinopyrimidine-3-oxide) and its derivatives, diazoxide (7-chloro-3-methyl-1,2,4-benzothiadiazine 1,1-dioxide) and phenyloin (5,4-diphenylimidazoline-2,4-dione); non-steroidal anti-inflammatories, carotenoids, in particular β-carotene; anti-psoriatic agents such as anthralin and its derivatives, and finally eicosa-5,8,11,14-tetraenoic acid and eicosa-5,8,11-trienoic acid, esters thereof and amides thereof.

The compositions according to the invention may also contain preservatives, such as para-hydroxybenzoic acid esters, stabilizers, moisture regulators, emulsifiers, UV-A and UV-B screens, or antioxidants, such as alpha-tocopherol, butylhydroxyanisole or butylhydroxytoluene.

The present invention also features compositions combining at least one extract of a non-photosynthetic and non-fruiting filamentous bacterium cultured on a medium comprising at least one non-sulfurous mineral and/or thermal water with one or more other active agents, in particular selected from agents that act on the microcirculation.

The agents that act on the microcirculation (vasoprotector, vasoconstrictor) may be selected from flavonoids, ruscogenins, esculosides, escin extracted from horse chestnut, nicotinates, heperidine methyl chalcone, essential oils of lavender or of rosemary, and extracts of *Ammi visnaga*.

The amount of these active agents can vary to a large extent. In general, these active agents are present at a concentration ranging from 0.01% to 15%, and preferably from 0.05% to 10% by weight, relative to the total weight of the composition.

The compositions according to the invention may also constitute a colored cosmetic composition, and in particular a composition for making up the skin, keratin fibers (hair or eyelashes) and/or mucous membranes, in particular a foundation, a blusher, a face powder or an eyeshadow, a lipstick or a lip gloss, optionally having care or treatment properties. Preferably, it may be a colored (beige or green) makeup composition for correcting the color of the complexion, and more particularly fading out or concealing the red blotches.

The expression "tinted composition masking red blotches according to the invention" means preferably a green-colored tinted composition. The compositions according to the invention then comprise one or more dyes so as to give the composition the desired green tint. The concept of the green tint is selected according to the color opposition principle symbolized by the chromatic circle. The intensity of the color may be reduced by the addition of its opposite color on the chromatic circle on which all colors are represented, each having its opposite. In all the artistic fields, the only way of neutralizing a color spot is to mix it with its opposite. Since green is opposite red on the chromatic circle, it is a green tint which is selected to color the composition according to the invention so as to neutralize the diffuse red blotches on the skin.

In order to provide the composition according to the invention the desired green tint, dyes are incorporated into the composition.

The term "dye" means the generic term used by those skilled in the art, defining a substance that gives a medium a color (article by Gisbert Otterstätter: "Coloring Cosmetics, Cosmetics & Toiletries magazine, vol. 111, March 1996, page 25-33), such as:

dyes defined as soluble in the medium to be colored, they are commonly liposoluble or water-soluble, colored pigments or lakes that are generally insoluble in the medium to be colored, the lakes being obtained by precipitation of water-soluble dyes with a water-insoluble salt such as aluminum hydroxide, water-dispersible pigments which, by addition of a solvent, give dispersions that are stable in water, allowing them to be used as dyes, taken alone or as a mixture.

Examples of dyes according to the invention include pigments such as brown, yellow or red iron oxides or hydroxides, chromium oxides or hydroxides, titanium oxides or hydroxides, mixtures of blue and yellow dyes such as the lakes referenced FD&C Blue No. 1 aluminum Lake (E133), FD&C Blue No. 2 aluminum Lake (E132), FD&C Yellow No. 5 Aluminum Lake (E102) or FD&C Yellow No. 6 Aluminum Lake (E110).

The dyes according to the invention may be used alone or as a mixture in order to give the composition according to the invention the desired green tint.

According to a preferred embodiment of the invention, the composition also comprises titanium oxides along with other dyes, for their covering property.

The dyes selected according to the invention should also be compatible with application to the skin and the mucous membranes, without inducing any adverse effect.

The compositions according to the invention preferably contain a total amount of dyes ranging from 0.001% to 10% by weight of the composition, it being understood that, preferably, the total amount of dyes may not exceed 1% by weight of the composition. Each dye is used in proportions ranging from 0.0001% to 1% by weight of the composition.

The preferred dye mixtures for the compositions according to the invention are the following:

FD&C blue No. 2 aluminum lake+yellow iron oxide+titanium dioxide;

chromium hydroxide+yellow iron oxide+titanium dioxide;

FD&C blue No. 1 aluminum lake+yellow iron oxide+titanium dioxide;

chromium hydroxide+titanium dioxide.

In another embodiment of the invention, the extract of a non-photosynthetic and non-fruiting filamentous bacterium cultured on a medium comprising at least one non-sulfurous mineral and/or thermal water is combined with an active agent useful for treating rosacea.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Preparation of a Bacterial Extract According to the Invention: Biomass of *Vitreoscilla Filiformis* Cultured on a Medium Enriched with Thermal Water from La Roche Posay Preparation of the Culture Medium:
Composition:

| | |
|---|---|
| Yeast extract | 2 to 3 g |
| Soybean papain peptone | 2 to 3 g |
| Glucose | 2 to 3 g |
| Heller microelements | 2 ml |
| $CaCl_2 \cdot 2H_2O$ | 66.21 mg |
| La Roche Posay thermal water | 13-14 ml. |

This stock solution will be diluted with osmosed water in a ratio of 1/75 before sterilization.

The pH of the medium is adjusted to 5.00 by adding a molar solution of $H_3PO_4$. The medium is sterilized by autoclaving at 121° C. for 30 minutes. After cooling to ambient temperature, the pH is readjusted to 7.20 by adding a molar solution of KOH.

Culturing:

After the medium has been inoculated at 1% with the *Vitreoscilla filiformis* strain, the culture is shaken on an orbital shaker at 100 rpm and at 26° C. After growth for 48 hours, the culture is centrifuged at 8,000 g for 15 minutes. The pellets are recovered and then autoclaved at 121° C. for 30 minutes. This biomass can be used for evaluation tests.

EXAMPLE 2

Activity of the Bacterial Extract According to the Invention (Biomass of *Vitreoscilla Filiformis* Cultured on a Medium Enriched with Thermal Water from La Roche Posay)

Experimental Conditions:

The measurement of the activity of 4 products: biomass of *Vitreoscilla filiformis* cultured on a medium supplemented with Sr, Se and Zn (D8), biomass of *Vitreoscilla filiformis* cultured on a medium enriched with thermal water from La Roche Posay (B51 prepared according to Example 1), biomass of *Vitreoscilla filiformis* cultured on an osmosed $H_2O$ medium (A28) and biomass of *Vitreoscilla filiformis* cultured on a medium supplemented with Sr (E1), is evaluated on a human skin explant under survival conditions, to which substance P is administered.

Skin Preparation:

8 human skins from different donors were obtained from women (from 25 and 50 years old) after consent, after plastic surgery, and maintained under survival conditions ex vivo.

The skin fragments were placed in inserts which were themselves suspended above culture wells. Medium (Dulbecco's minimum essential medium, D-MEM) (antibiotics, SVF) was added to the bottom of the wells, with there being movement by slow diffusion from the two compartments by means of a porous membrane (0.45 mm). 5 hours of re-equilibration are required before beginning the protocol.

Application of the Nutritive Medium and Experimental Model of Neurogenic Inflammation Using Substance P:

After the 5 hours of re-equilibration, the products were added, as a pretreatment, to the D-MEM culture medium at the concentration of 30%. The skin fragments were then maintained in organ culture for 24 hours in an incubator with a humid atmosphere, at 37° C. and in the presence of 5% $CO_2$.

At D1, the experimental model of neurogenic inflammation was realized by adding 10 μM of substance P (SP) to the culture medium. The nutritive media were renewed and a further 24 hours of incubation were carried out for all the conditions.

A comparative study was thus carried out from the following 6 conditions:

Model of Stimulation with SP in Comparison with Control Skin:

control skin (basic condition: non-stimulated, non-treated skin) with D-MEM medium, skin stimulated with substance P at 5 μM in D-MEM medium, skin stimulated with substance P at 5 μM in D-MEM medium+B51, skin stimulated with substance P at 5 μM in D-MEM medium+E1, skin stimulated with substance P at 5 μM in D-MEM medium+A28, skin stimulated with substance P at 5 μM in D-MEM medium+D8.

Analyses:

The skin fragments were fixed in Bouin's solution and embedded in paraffin.

Histological Evaluation of Mast Cell Degranulation:

The mast cells present in the dermis were revealed in blue-violet by staining with toluidine blue. Histologically, a more or less intense blue-violet and granular appearance of the mast cells in relation to the more or less substantial presence in their cytoplasm of basophilic and metachromatic granulations containing in particular histamine was observed.

The mast cells were then counted under an optical microscope (15 fields at ×40 magnification, on 3 planes of section), categorizing them using the following 3 scores:

score 3: highly basophilic cells with the presence of intense blue-violet staining covering the entire cytoplasm or preferentially located at one pole of the cell (mast cells containing a large number of basophilic granulations);

score 2: cells with moderate and homogeneous staining throughout the cytoplasm of the cell, or comprising a weak blue-violet halo located at the periphery of the cell (mast cells containing a moderate number of basophilic granulations);

score 1: degranulated mast cells with disappearance of the blue-violet staining of the cytoplasm or persistence of a few rare grains arranged sparsely in the cytoplasm (mast cells containing a small number of basophilic granulations).

The degranulation obtained after application of substance P is responsible for a decrease in or an absence of toluidine-blue staining of the mast cells. This decrease in staining is in relation to a decrease or a virtually complete disappearance of the number of granulations initially present in the cytoplasm of the mast cells.

The results were expressed in the following way: for each individual, the percentage of mast cells having each score was calculated relative to the total number of mast cells.

Statistical Analyses:

A mean was calculated from the results obtained on the 8 skins. The statistical analysis is carried out using the Student's test referred to as Z-score, or paired sample test, with a risk α of 5%.

Results:

Histological Evaluation of Mast Cell Degranulation:

In the model of skin maintained under survival conditions, stimulated with SP, a statistically significant decrease in the % of highly granulated mast cells (score 3) was observed: 40% versus 80% in the control skins (FIG. 1 hereinafter; p<0.05). Substance P therefore has a mast cell degranulation effect.

No significant difference from the % of mast cells having the score of 3 was observed in the "SP+B51" condition and that observed in the "control" condition (score of 75% versus 80%).

This lack of difference attests to a protective effect of the extract used according to the invention (B51) with respect to substance P-induced degranulation.

A protection induced by the products E1, A28 and D8 is also observed, but it is considerably less substantial than that objectified for the product B51.

The FIGURE of Drawing shows that the 4 preparations are statistically different in comparison with the skin explant treated with substance P. The B51 fraction is the only one which restores a normal function. *p<0.05 versus treated skin/#p<0.05 versus skin treated with substance P

: statistically significant difference relative to the same condition without SP (Student's paired test, p<0.05).

*: statistically significant difference relative to the control (Student's paired test, p<0.05).

Conclusion:

In this model of human skin maintained under survival conditions, an anti-inflammatory effect of the B51 fraction that can be used according to the invention was demonstrated.

EXAMPLE 3

Clinical Trials

Clinical Data:

A first clinical study (study 1), double blind, evaluated, intra-individually, the comparative effect of a cream containing 5% of extract of *Vitreoscilla filiformis* (V.f.) cultured conventionally (hereinafter referred to as "conventional extract") on the red blotches occurring in individuals suffering from slight to moderate atopic dermatitis (symmetrical lesions against placebo).

The "conventional" extract of *Vitreoscilla filiformis* is prepared according to the following modes:

Preparation of the Culture Medium:

Composition:

| Yeast extract | 2 g |
| Soybean papain peptone | 2 g |
| Glucose | 2 g |
| Heller microelements | 2 ml |
| $CaCl_2 \cdot 2H_2O$ | 66.21 mg |
| Water | qs 1 l. |

The pH of the medium is then adjusted to 5.00 by adding a molar solution of $H_3PO_4$. The medium is sterilized by autoclaving at 121° C. for 30 minutes. After cooling to ambient temperature, the pH is readjusted to 7.20 by adding a molar solution of KOH.

Culturing:

In the laboratory: After inoculation of the medium at 1% with the *Vitreoscilla filiformis* strain, the culture is shaken on an orbital shaker at 100 rpm and at 26° C. After growth for 48 hours, the culture is centrifuged at 8,000 g for 15 minutes. The pellets are recovered and then autoclaved at 121° C. for 30 minutes. This biomass can be used for evaluation tests.

In fermenter: a fermenter preferably equipped with a draft tube in order to limit the shear force is inoculated with the *Vitreoscilla filiformis* strain at a minimum of 1% volume. The pH is maintained stable at 7 UpH throughout the culturing, the temperature is adjusted from 26 and 28° C. and the oxygenation is maintained at 10% $PO_2$ throughout the culturing, either by action on the shaking speed or by adjustment of the airflow rate. This type of culturing can be carried out as a batch, fed-batch or continuous culture. The latter technique is preferred since it guarantees a reproducible biomass through controlling the growth rate (μ). The biomass harvested continuously by centrifugation at 10,000 g is frozen at −20° C. When the freezing tank is full, it is thawed at 4° C. and then packaged in packages that can be handled by an operator. These packages containing the biomass are then sterilized so as to be stabilized. Each sterilization operation then is a production batch.

In this study, the composition comprising the bacterial extract referred to as "conventional extract" is applied twice a day and was very well tolerated.

The extract is formulated in composition 1A, which is a formula containing 5% of the conventional extract in an oil-in-water/Arlacel/Myrj emulsion containing 5% parleam and 15% volatile silicone. The effect of this composition 1A is compared with that of a placebo. Composition 2A which corresponds to the excipient: oil-in-water/Arlacel/Myrj emulsion containing 5% parleam and 15% volatile silicone.

This composition 1A containing the "conventional" extract of *Vitreoscilla filiformis* at 5% has no significant effect on decreasing the erythema of the skin of the individuals tested.

Conversely, in a second study (study 2 carried out under the same conditions as the previous study, by the same team of experimenters), the composition containing 5% of extract of *Vitreoscilla filiformis* cultured on a medium enriched with thermal water from La Roche Posay (prepared according to Example 1) also demonstrated a specific effectiveness on the erythema and therefore on the vascular valency of the condition.

The extract is formulated in composition 1B, which is a formula containing 5% of bacterial extract according to the invention (obtained according to Example 1) in an Arlacel/Myrj oil-in-demineralized water emulsion containing 5% parleam, 15% cyclopentasiloxane, 3% glycerol and 2% petroleum jelly. The effect of this composition 1B is compared with that of a placebo: composition 2B which corresponds to an Arlacel/Myrj oil-in-water from La Roche Posay emulsion containing 5% parleam, 15% cyclopentasiloxane, 3% glycerol and 2% petroleum jelly.

The therapeutic efficacy was observed for the 15 days following application.

Thus, the bacterial extracts cultured on water from La Roche Posay of composition 1B, unlike the known bacterial extracts, significantly decreased the erythema of the individuals on the areas where they were treated, in comparison with the effect of the contra-lateral placebo (p=0.02, Fisher test).

EXAMPLE 4

Formulations Examples

Cream Formula:

| Phases | Constituents | % (w/w) |
|---|---|---|
| A1 | Purified water | QS 100% |
| A1 | Glycerol | 4.00 |
| A1 | Sorbitol | 5.00 |
| A2 | Metronidazole | 0.75 |
| A3 | Bacterial extract according to the invention | 5 |
| B1 | Isopropyl palmitate | 2.00 |
| B1 | Self-emulsifiable wax | 12.50 |
| B2 | Yellow iron oxide | 0.0045 |
| B2 | Green chromium oxide | 0.020 |
| B3 | Titanium dioxide | 0.50 |
| C | Benzyl alcohol | 2.20 |
| D | 90% lactic acid | Qs pH 5 |

Phase Preparation—Procedure:
Fatty Phase B:

The self-emulsifiable wax is solubilized, at 75° C., with stirring (weak Rayneri stirring), in the isopropyl palmitate (B1) so as to obtain a clear homogeneous phase.

The yellow pigment is then introduced, with Rayneri stirring, followed by the green pigment (B2) and the titanium dioxide (B3). The mixture is dispersed for 30 min (moderate Rayneri stirring) so as to obtain a homogeneous green phase.

Aqueous Phase A:

The glycerol and the sorbitol (A1) are homogenized, at 75° C., in the purified water with stirring (weak Rayneri stirring).

The metronidazole (A2) is then introduced and it is verified that it has completely dissolved.

An emulsion is prepared at 75° C. by introducing phase B (B1+B2) into phase A (moderate Rayneri stirring), and this temperature is maintained for 10 min.

The emulsion is cooled to 45° C. The benzyl alcohol is introduced with stirring (moderate Rayneri stirring), and the whole is homogenized.

The mixture is cooled to 25° C. with stirring, the pH is measured and if necessary it is adjusted, qs pH 5.

This procedure results in the production of a cream that is light green in color.

Lotion Formula:

| Phases | Constituents | % (w/w) |
|---|---|---|
| A1 | Purified water | QS 100% |
| A1 | Glycerol | 7.00 |
| A2 | Carbomer 981 | 0.15 |
| A3 | PEG 400 | 2.00 |
| A4 | Steareth 21 | 3.00 |
| A5 | Metronidazole | 0.75 |
| A6 | Bacterial extract according to the invention | 5% |
| B1 | Yellow iron oxide | 0.0045 |
| B1 | Green chromium oxide | 0.02 |
| B1 | Titanium dioxide | 0.50 |
| B1 | Mineral oil | 6.00 |
| B2 | Glyceryl & PEG 100 stearate | 3.00 |
| B2 | Stearyl alcohol | 2.00 |
| C | Benzyl alcohol | 1.30 |
| D | Purified water | 2.00 |
| D | Potassium sorbate | 0.20 |
| E | Cyclomethicone 5 | 4.00 |
| F | 10% sodium hydroxide solution | Qs pH 5 |
| F | Solution containing 1% of lactic acid (90%) | Qs pH 5 |

Phase Preparation—Procedure:
Fatty Phase B:

The yellow and green pigments are dispersed, at 80° C., with stirring for 15 min, in the mineral oil (moderate Rayneri stirring). The titanium dioxide is then introduced, and the mixture is homogenized for 15 min.

The temperature is maintained at 80° C., and then the glyceryl and PEG 100 stearate and the stearyl alcohol (B2) are introduced and the mixture is homogenized until complete solubilization of the waxes, so as to obtain a homogeneous green phase.

Phase D:

The potassium sorbate is solubilized in the purified water.
Aqueous Phase A:

The carbomer 981 is dispersed, at 80° C. (moderate Rayneri speed), in the purified water and the glycerol.

The PEG 400 (A3) and the steareth 21 (A4) are introduced and the mixture is homogenized for 5 min.

The metronidazole (A5) is then introduced and it is verified that it has completely dissolved.

An emulsion is prepared at 80° C. by introducing fatty phase B into aqueous phase A with stirring (moderate Rayneri stirring). The emulsion is homogenized for 10 min.

The emulsion is cooled.

Phases C, D and E are introduced at 40° C.

The mixture is cooled to 25° C., with stirring, and the pH is measured and adjusted, if necessary, qs pH 5, with the solution of sodium hydroxide at 10% or lactic acid at 1%.

The procedure results in the production of a gel fluid which is light green in color.

Cream Formula:

| Phases | Constituents | % (w/w) |
|---|---|---|
| A1 | Purified water | QS 100% |
| A1 | Glycerol | 4.00 |
| A1 | Sorbitol | 5.00 |
| A2 | Metronidazole | 0.75 |
| A3 | Bacterial extract according to the invention | 2 |
| B1 | Isopropyl palmitate | 2.00 |
| B1 | Self-emulsifiable wax | 12.50 |
| B2 | Yellow iron oxide | 0.0095 |
| B2 | FD&C Blue Aluminum Lake | 0.0068 |
| B3 | Titanium dioxide | 0.50 |
| C | Benzyl alcohol | 2.20 |
| D | 90% lactic acid | Qs pH 5 |

Aqueous Phase:

The glycerol, the sorbitol, the benzyl alcohol and the purified water are weighed into a beaker. The metronidazole is then introduced.

The phase is heated to 75° C. and then the active agent is solubilized with moderate stirring for 20 minutes.

Fatty Phase:

The self-emulsifiable wax and the isopropyl palmitate are weighed into a beaker. The phase is heated to 75° C., and is homogenized with stirring using an ultra-turrax. The pigments weighed out together and the titanium dioxide are then introduced with stirring on an ultra-turrax at 8,000 rpm for at least 20 minutes.

Emulsification and Cooling:

An emulsion is prepared at 75° C. for 10 minutes with moderate Rayneri stirring by introducing the fatty phase into the aqueous phase.

The emulsion is cooled with gentle stirring.

A thick homogeneous green cream is obtained.

Cream Formula:

| Phases | Constituents | % (w/w) |
|---|---|---|
| A1 | Purified water | QS 100% |
| A1 | Glycerol | 4.00 |
| A1 | Sorbitol | 5.00 |
| A3 | Bacterial extract according to the invention | 5 |
| B1 | Isopropyl palmitate | 2.00 |
| B1 | Self-emulsifiable wax | 12.50 |
| B2 | Yellow iron oxide | 0.0045 |
| B2 | Green chromium hydroxide | 0.020 |
| B3 | Titanium dioxide | 0.50 |
| C | Benzyl alcohol | 2.20 |
| D | 90% lactic acid | Qs pH 5 |

The procedure is the same as that for the previous formulation.

Cream Formula:

| Phases | Constituents | % (w/w) |
|---|---|---|
| A1 | Purified water | QS 100% |
| A1 | Glycerol | 4.00 |
| A1 | Sorbitol | 5.00 |
| A3 | Bacterial extract according to the invention | 5 |
| B1 | Isopropyl palmitate | 2.00 |
| B1 | Self-emulsifiable wax | 12.50 |
| B2 | Yellow iron oxide | 0.019 |
| B2 | FD&C Blue Aluminum Lake | 0.0136 |
| B3 | Titanium dioxide | 1.00 |
| C | Benzyl alcohol | 2.20 |
| D | 90% lactic acid | Qs pH 5 |

The procedure is the same as that for the previous formulation.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method of treating erythema in a human suffering from atopic dermatitis and/or erythema in a human suffering from seborrheic dermatitis, the method comprising administering an effective amount of an extract of *Vitreoscilla filiformis* to the human in need thereof to treat the erythema in a human suffering from atopic dermatitis and/or the erythema in a human suffering from seborrheic dermatitis, wherein the *Vitreoscilla filiformis* is cultured in a medium which comprises at least one non-sulfurous mineral and/or thermal water.

2. The method of claim 1, wherein said thermal water is from La Roche Posay.

3. The method of claim 1, wherein said at least one non-sulfurous mineral and/or thermal water has a total mineral content ranging from 400 to 900 mg/l.

4. The method of claim 1, wherein said at least one non-sulfurous mineral and/or thermal water has a total concentration of carbonates and of bicarbonates of at least 150 mg/l and a concentration of silicon oxide of at least 6 mg/l.

5. The method of claim 1, wherein said thermal water is from Vittel, from the Vichy basin, from Uriage, from La Bourboule, from Enghien-les-Bains, from Saint-Gervais-les-Bains, from Néris-les-Bains, from Allevard-les-Bains, from Digne, from Maizières, water from Neyrac-les-Bains, from Lons-le-Saunier, from Eaux-Bonnes, from Rochefort, from Saint Christau, from Les Fumades or from Tercis-les-Bains.

6. The method of claim 3, wherein said at least one non-sulfurous mineral and/or thermal water has a concentration of calcium ions of at least 100 mg/l.

7. The method of claim 1, said *Vitreoscilla filiformis* extract is from 0.001 to 20% by weight of the total weight of a composition comprised thereof.

8. The method of claim 1, further comprising administering to said human at least one agent selected from the group consisting of retinoids, corticosteroids, free-radical scavengers, alpha-hydroxy, alpha-keto acids, ion channel blockers, wetting agents, depigmenting agents, emollients, moisturizers, anti-seborrheic, anti-acne agents, antibiotics, anti-fungal agents, agents for promoting hair regrowth, non-steroidal anti-inflammatories, carotenoids, anti-psoriatic agents, preservatives, stabilizers, moisture regulators, emulsifiers, ultraviolet A screens, ultraviolet B screens, and antioxidants.

9. The method of claim 1, further comprising administering to said human at least one agent selected from the group consisting of vasoprotector agents that act on the microcirculation, vasoconstrictor agents that act on the microcirculation, a substance that gives the skin a color, and an active agent for treating rosacea.

10. The method of claim 9, further comprising administering to said human a green colorant.

11. The method of claim 1, wherein the culture medium consists essentially of water from La Roche Posay, autolyzed yeast extract, plant peptone, anhydrous glucose, Heller microelements and calcium chloride.

\* \* \* \* \*